(12) United States Patent
Amara et al.

(10) Patent No.: US 9,138,472 B2
(45) Date of Patent: Sep. 22, 2015

(54) CD40L VACCINES, COMPOSITIONS, AND METHODS RELATED THERETO

(75) Inventors: Rama Rao Amara, Decatur, GA (US); Lilin Lai, Decatur, GA (US); Sue Fen Kwa, Decatur, GA (US)

(73) Assignee: EMORY UNIVERSITY, Atlanta, GA (US)

( * ) Notice: Subject to any disclaimer, the term of this patent is extended or adjusted under 35 U.S.C. 154(b) by 71 days.

(21) Appl. No.: 13/247,484

(22) Filed: Sep. 28, 2011

(65) Prior Publication Data

US 2012/0076820 A1    Mar. 29, 2012

Related U.S. Application Data

(60) Provisional application No. 61/387,417, filed on Sep. 28, 2010.

(51) Int. Cl.
*A61K 39/21* (2006.01)
*A61K 39/12* (2006.01)
*A61K 39/00* (2006.01)

(52) U.S. Cl.
CPC .............. *A61K 39/21* (2013.01); *A61K 39/12* (2013.01); *A61K 2039/5256* (2013.01); *A61K 2039/5258* (2013.01); *A61K 2039/53* (2013.01); *A61K 2039/545* (2013.01); *A61K 2039/55516* (2013.01); *A61K 2039/57* (2013.01); *C12N 2740/15023* (2013.01); *C12N 2740/15034* (2013.01); *C12N 2740/16134* (2013.01); *C12N 2740/16234* (2013.01); *C12N 2810/855* (2013.01)

(58) Field of Classification Search
None
See application file for complete search history.

(56) References Cited

U.S. PATENT DOCUMENTS

| | | |
|---|---|---|
| 2006/0051839 A1 | 3/2006 | Robinson |
| 2007/0048861 A1 | 3/2007 | Robinson |
| 2009/0092635 A1 | 4/2009 | Clarke |
| 2013/0280215 A1 | 10/2013 | Robinson |

OTHER PUBLICATIONS

Lin et al., Journal of Virology, Feb. 2009, 83(3):1216-1227.*
Wong et al., Gene Therapy, 2002, 9:337-344.*
Zhang et al., Vaccine, 2010, 28:5114-5127.*
Litzinger et al., Leukemia Research, 2010, 34:1351-1357.*
Liu et al., Vaccine, 2008, 26:4062-4072.*
Yao et al., Aids Research and Human Retroviruses, 2000, 16(3):227-236.*
Jin et al., Journal of Virology, Mar. 2002, 76(5):2206-2216.*
Scriba et al., Vaccine, 2005, 23:1158-1169.*
Zhang et al., Journal of Surgical Research, Oct. 2003, 114(2):280.*
Kannanganat et al., Single-Cytokine-Producing Cells T Cells Are Functionally Superior to Multiple-Cytokine Producing Antiviral CD4, J. Virol. 2007, 81(16):8468.
Kwa et al., Heterologous SIVE660 Mucosal Challenge and Improves Protection against a SIV-Specific Humoral and Cellular Immunity Virus SIV239 Vaccine Enhances Virus Ankara Simian Immunodeficiency CD40L-Adjuvanted DNA/Modified Vaccinia, J. Virol. 2014, 88(17):9579.
Lai et al., Prevention of Infection by a Granulocyte-Macrophage Colony-Stimulating Factor Co-Expressing DNA/Modified Vaccinia Ankara Simian Immunodeficiency Virus Vaccine, JID (2011) 204:165-173.
Lai et al., SIVmac239 MVA vaccine with and without a DNA prime, similar prevention of infection by a repeated dose SIVsmE660 challenge despite different immune responses, Vaccine 30 (2012) 1737-1745.
Robinson et al. Immunogenicity in Macaques of the Clinical Product for a Clade B DNA/MVA HIV Vaccine: Elicitation of IFN-, IL-2, and TNF—Coproducing CD4 and CD8 T Cells, Aids Research and Human Retroviruses, 2007 23(12):555-1561.
Tahara et al. Trans-splicing repair of CD40 ligand deficiency results in naturally regulated correction of a mouse model of hyper-IgM X-linked immunodeficiency, Nature Medicine, 2004, 10(8):835-841.
Tang et al, Use of CD4OL immunoconjugates to overcome the defective immune response to vaccines for infections and cancer in the aged, Cancer Immunol Immunother (2009) 58:1949-1957.
Wierda et al., CD40-ligand (CD154) gene therapy for chronic lymphocytic leukemia, Blood, 2000, 96:2917-2924.
Wyatt et al., Multiprotein HIV Type 1 Clade B DNA and MVA Vaccines: Construction, Expression, and Immunogenicity in Rodents of the MVA Component AIDS Research and Human Retroviruses, 2004, 20(6):645-653.
Robinson, Prime boost vaccines power up in people, Nature Medicine 9, 642-643 (2003).
Xin et al., Prime-boost vaccination with plasmid DNA and a chimeric adenovirus type 5 vector with type 35 fiber induces protective immunity against HIV, Gene Therapy (2005) 12, 1769-1777.
Amara et al. Different patterns of immune responses but similar control of a simian-human immunodeficiency virus 89.6P mucosal challenge by modified vaccinia virus Ankara (MVA) and DNA/MVA vaccines. J Virol 2002; 76: 7625-7631.

* cited by examiner

*Primary Examiner* — Nicole Kinsey White
(74) *Attorney, Agent, or Firm* — Emory Patent Group

(57) ABSTRACT

The disclosure relates to vaccinating a subject against a viral infection, compositions, and methods related thereto. In certain embodiments, the disclosure relates to the use of CD40L expressed on viral like particle as an adjuvant, in combination with a viral antigen, to vaccinate a subject.

6 Claims, 6 Drawing Sheets

SEQUENCE LISTING

```
<160> NUMBER OF SEQ ID NOS: 1

<210> SEQ ID NO 1
<211> LENGTH: 261
<212> TYPE: PRT
<213> ORGANISM: Homo sapiens

<400> SEQUENCE: 1

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
        50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140
```

-continued

```
Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
                180                 185                 190

Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
            210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
             260
```

CD40L VACCINES, COMPOSITIONS, AND METHODS RELATED THERETO

CROSS REFERENCE TO RELATED APPLICATIONS

This application claims priority to U.S. Provisional Patent Application Ser. No. 61/387,417, filed Sep. 28, 2010, which is hereby incorporated by this reference in its entirety.

ACKNOWLEDGEMENTS

This invention was made with government support under Grant R01 AI071852 awarded by the National Institute of Health. The government has certain rights in the invention.

BACKGROUND OF THE INVENTION

The World Health Organization estimates that AIDS has killed more than 25 million people since it was first recognized. In 2007 there were 2.7 million new HIV infections and 2 million HIV-related deaths. Many chronic viral infections are caused by retroviruses. For certain chronic viral infections, the immune system cannot clear the virus from the host even with the aid of therapeutic agents. For example, although highly active anti-retroviral therapy (HAART) may improve symptoms associated with infection, there is currently no cure for HIV or vaccine, and methods of preventing infections would be desirable.

Recombinant modified vaccinia virus Ankara (MVA) expressing SIV or HIV Gag-Pol and Env was described for managing immunodeficiency virus infections in nonhuman primates. Wyatt et al., (2004) AIDS Res Hum Retroviruses 20(6):645-53. This vaccine elicits a good CD4 T-cell response but a relatively weak CD8 T-cell response. It is desirable to improve the ability of the vaccine to elicit a stronger CD8 response since CD4 cells are preferentially infected by the HIV virus.

Clinical trials using CD40L to induce immune responses has been described. Tahara et al., (2004) Nat Med 10:835-841. Insertion of the CD40L gene into the transcription units of replication incompetent adenoviral vectors has been reported. Wierda et al., (2000) Blood 96:2917-2924. A chimeric molecule composed of a target antigen linked to the extracellular domain (ecd) of the CD40L has been described. Tang et al., (2009) Cancer Immunol Immunother 58(12):1949-57.

SUMMARY

The disclosure relates to vaccinating a subject against a viral infection, compositions, and methods related thereto. It is desirable to express CD40L in a certain form to achieve desirable adjuvant activity. In certain embodiments, the disclosure relates to the use of CD40L as an adjuvant, in combination with a viral antigen, to vaccinate a subject. In certain embodiments, the disclosure relates to methods of treating or preventing a viral infection comprising administering to a subject at risk of a viral infection a recombinant vector comprising genes sufficient to produce a viral-like particle and a nucleic acid sequence that encodes CD40L. In further embodiments, the viral like particle comprises CD40L.

In certain embodiments, CD40L is encoded in a nucleic acid that is expressed by a recombinant vector. In certain embodiments, the CD40L is expressed on the surface of the viral like particle in combination with a viral antigen.

In certain embodiments the disclosure relates to a recombinant Modified Vaccinia Ankara (MVA) virus comprising genes sufficient to produce a viral like particle and a nucleic acid sequence that encodes CD40L. In further embodiments, the recombinant Modified Vaccinia Ankara (MVA) virus comprises an HIV env gene. Typically the viral like particle comprises is an envelope protein. In further embodiments, the envelope protein is a lentiviral envelope protein, such as an SIV or HIV envelope protein.

In certain embodiments, the disclosure relates to viral vaccines and vaccinating using compositions disclosed herein. In certain embodiments, the viral vaccine is for the treatment or prevention of infection from a retrovirus.

In some embodiments, vaccine comprises an envelope protein or capsid from influenza A virus including subtype H1N1, influenza B virus, influenza C virus, rotavirus A, rotavirus B, rotavirus C, rotavirus D, rotavirus E, SARS coronavirus, human adenovirus types (HAdV-1 to 55), human papillomavirus (HPV) Types 16, 18, 31, 33, 35, 39, 45, 51, 52, 56, 58, 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, respiratory syncytial virus, rinderpest virus, California encephalitis virus, hantavirus, rabies virus, ebola virus, marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, Kaposi's sarcoma-associated herpesvirus, hepatitis A (HAV), hepatitis B (HBV), hepatitis C (HCV), hepatitis D (HDV), hepatitis E (HEV), human immunodeficiency virus (HIV), The Human T-lymphotropic virus Type I (HTLV-1), Friend spleen focus-forming virus (SFFV) or Xenotropic MuLV-Related Virus (XMRV).

In certain embodiments, the recombinant vector is replication competent. In certain embodiments, the recombinant vector is replication incompetent.

In some embodiment, the recombinant vector further comprises a nucleic acid that encodes a viral matrix protein or a viral core protein or a reverse transcriptase, proteases, ribonuclease or integrase or a gag, pol, or env, viral gene or a tat or rev viral gene. In certain embodiments the vector does not encode an integrase.

In certain embodiments, the vector comprises a nucleotide sequence that allows for translation initiation in the middle of a messenger RNA (mRNA) sequence operably linked to a nucleic acid sequence that encodes CD40L such as an internal ribosome entry site (IRES). In certain embodiment, the disclosure relates to an isolated composition comprising a nucleic acid that encodes a CD40L and a nucleic acid that encodes the envelope protein of a virus.

DETAILED DESCRIPTIONS

Figure 1:
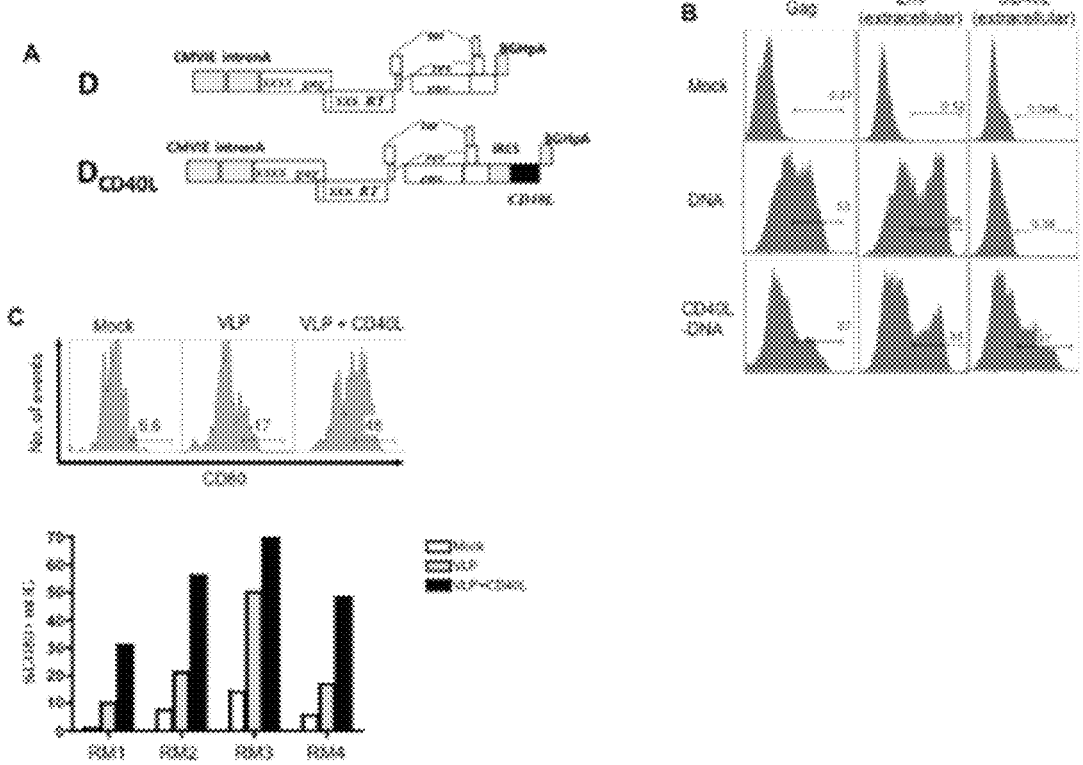
FIG. 1 illustrates certain embodiments of the disclosure. A) Construct diagram of DNA and CD40L DNA vaccines. DNA immunogens expressed are SIVmac239 gag, env, rev, tat sequences which are driven by the CMV early intermediate intron A promoter and stabilized by a BGH polyadenylation sequence. The CD40L DNA vaccine comprises the same structure as the DNA vaccine but includes the IRES-driven macaque CD40L sequence inserted in the Nef region. B) Expression levels of Gag, envelope and CD40L proteins in 293T cell lines transfected with the DNA or DNA-CD40L DNA plasmids using flow cytometric analysis. C) Effect of virus-like particles (VLPs) on dendritic cells. FACS plots show the upregulation of CD80 on CD11c+mDC after addition of VLPs with and without CD40L. Mock indicates supernatant used from a transfection carried out without DNA. Bar chart shows 4 individual macaques where the use of VLPs show increased CD80 expression on myeloid dendritic cells.

Studies disclosed herein suggest that CD40L expressed on VLP enhances the avidity of vaccine elicited humoral immunity and there by enhances protection against a pathogenic immunodeficiency virus infection.

Dendritic cells (DCs) are antigen presenting cells (APCs) which play a role in the induction of adaptive immune responses. DCs internalize extracellular antigens and present antigen-derived peptides in the context of MHC molecules to T cells. Recognition of these complexes by antigen-specific CD4 Th cells is important for full activation of macrophages, B cells, and CD8 T cells in vivo. DCs are capable of presenting extracellular antigens on MHC class I (MHC I) molecules, a process termed cross-presentation, that enables DCs to activate antigen-specific cytotoxic CD8 T cells. Cross presentation involves co-stimulation of DCs with CD4 and via interaction between CD40L expressed on CD4 cells and CD40 expressed on DCs. It may be that virus like particles elicit a poor CD8 response because of insufficient co-stimulation.

For certain embodiments, the disclosure relates to co-stimulation of DCs using CD40L. A DNA vaccine co-expressing SIV viral like particles and CD40L was developed. In vitro activation experiments using these viral like particles activated DCs suggesting that a vaccine may be developed to provide co-stimulatory signaling during cross-presentation of the vaccine antigen.

The CD40 Ligand (CD40L also known as CD154) belongs to the TNF family of ligands. The expression of CD40L on the surface of CD4 helper T cells is an activation signal of the adaptive immune response. Increasing the frequency of antigen-specific representation to CD8 effector T cells, or antigen-specific B cells is important in vaccination. Engagement of the CD40 receptor on dendritic cells (DCs) or antigen presenting cells and B cells by the CD40L on activated CD4 helper T cells effects activation and expansion of target-associated antigen (TAA)-specific CD8 effector cells and increases in the levels of TAA-specific antibodies by vaccination. CD40L binding to the CD40 receptor on the DCs promotes presentation of TAAs on Class I MHC molecules, and migration of the DCs to regional lymph nodes following antigen or virus exposure.

TERMS

The term "antigen" or "Ag" refers to a molecule that provokes an immune response. The immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present disclosure includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "vector" as used herein refers to a nucleic acid molecule which is capable of transferring nucleic acid sequences contained therein into a cell, and which is produced by means of molecular biological techniques. Recombinant vectors are exemplified by linear DNA, plasmid DNA, modified viruses, etc. Linear DNA, plasmid, adenovirus/adeno-associated viral, retroviral and viral vectors may be made using standard molecular biological techniques, or purchased and utilized as described by suppliers. A typical recombinant vector is selected from the group consisting of a lentiviral vector, an adnoviral vector and an ando-associated viral vector. A lentiviral vector refers to a recombinant vector bases on a lentivirus. HIV, SIV, and FIV are examples of lentiviruses.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene. A "coding region" of an mRNA molecule also consists of the nucleotide residues of the mRNA molecule which are matched with an anti-codon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "recombinant vector" as used herein is defined as vector produced by joining pieces of nucleic acids from different sources.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

The term "CD40L" refers to a macromolecule comprising a polypeptide sequence that binds CD40. In humans, CD40L is expressed on the surface of T cells. It regulates B cell function by engaging CD40 on the B cell surface. Human CD40L has the following amino acid sequence MIETYNQTSP RSAATGLPIS MKIFMYLLTV FLITQMIGSA LFAVYLHRRL DKIEDERNLH 61 EDFVFMKTIQ RCNTGERSLS LLNCEEIKSQ FEGFVKDIML NKEETKKENS FEMQKGDQNP 121 QIAAHVISEA SSKTTSVLQW AEKGYYTMSN NLVTLENGKQ LTVKRQGLYY IYAQVTFCSN 181 REASSQAPFI ASLCLKSPGR FERILLRAAN THSSAKPCGQ QSIHLGGVFE LQPGASVFVN 241 VTDPSQVSHG TGFTSFGLLK L (SEQ ID NO:1). It is contemplated that variant and mutant sequences such as isoforms and fragments will also bind to CD40. The term is contemplated to include naturally occurring polymorphs and comparable CD40L proteins produced by other organisms. Fragments may be of less than 200, 150, 100, 50, 40, 30 or 20 amino acids from the N terminal end, the C terminal end, or the middle or the polypeptide.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

EXPERIMENTAL

Example 1

Construction of DNA Vaccine Expressing CD40L on SIV VLPs

The DNA vaccine expressed SIV239 Gag-Pol, Env, Tat and Rev using a single CMV promoter and subgenomic splicing of mRNA that is used by the SIV, as described in Lai L et al. 2011 J Infect Dis. 204:164-73, hereby incorporated by reference. The CD40L DNA vaccine was generated by inserting a DNA fragment containing macaque CD40L gene fused to an internal ribosome entry site (IRES) containing DNA, just downstream of the SIV Env gene of the DNA/SIV plasmid (FIG. 1A). The CD40L DNA vaccine expressed SIV VLPs containing CD40L on them. The expression of these proteins was confirmed by flow cytometry (FIG. 1B) and the co-stimulatory activity of the CD40L-containing VLPs was confirmed by activating macaque dendritic cells in vitro followed by flow cytometry (FIG. 1C).

Example 2

Macaque Trial

In this study, Indian rhesus macaques were immunized with either DNA vaccine (n=8, all Mamu A*01 negative) or CD40L DNA vaccine (n=12, 6 Mamu A*01 negative and 6 Mamu A*01 positive). Two DNA primes were given on weeks 0 and 8. All animals were boosted with a MVA vaccine on weeks 16 and 24. The MVA vaccine also expressed SIV239 Gag, Pol and Env but did not express CD40L. Immune responses were measured after each vaccination. Results for Mamu A*01 positive and negative animals in the DNA/SIV-CD40L group were shown separately on the graphs.

Figure 2:
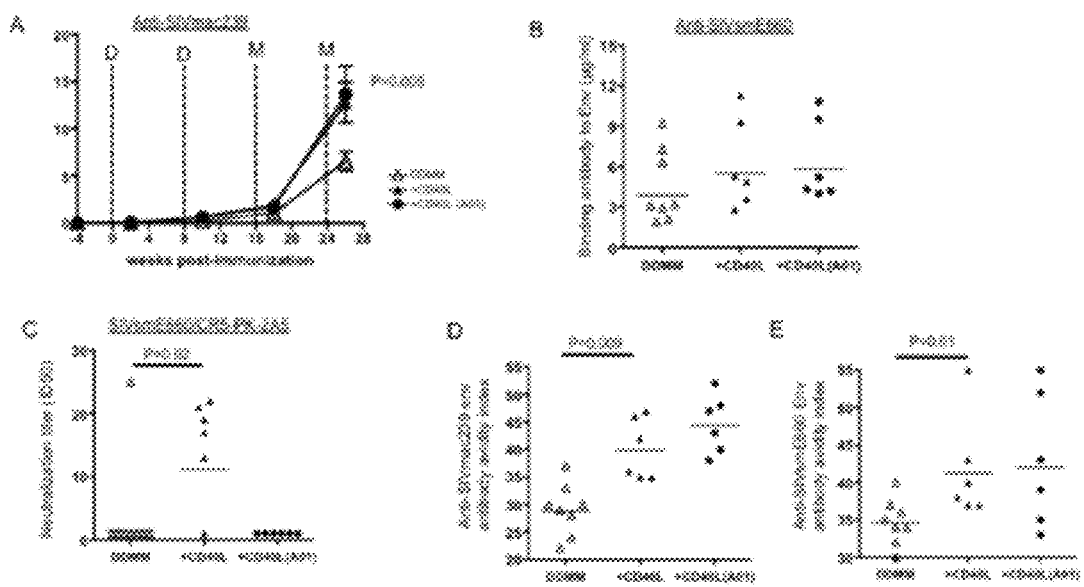
FIG. 2 shows data on Anti-SW antibody responses post-vaccination in rhesus macaques. A) Levels of binding antibody to the vaccine immunogen SIVmac239 Env pre- and post-vaccination. Macaques were given two DNA (D) and two MVA(M) immunizations at 8-wk intervals. The DDMM group received DNA vaccine and the +CD40L group received CD40L DNA vaccine. A01 indicates that these animals express Mamu A*01 histocompatibility molecule. B) Binding antibody titers to the challenge virus SIVsmE660 Env at 2 weeks post 2nd MVA boost. D) Levels of neutralization antibodies to tier 2 isolate (SIVsmE660/CRS-PK-2A5). D) Avidity index of antibodies to SIVmac239 Env and E) to SIVsmE660 Env at 2 weeks post 2nd MVA boost.
Figure 3:
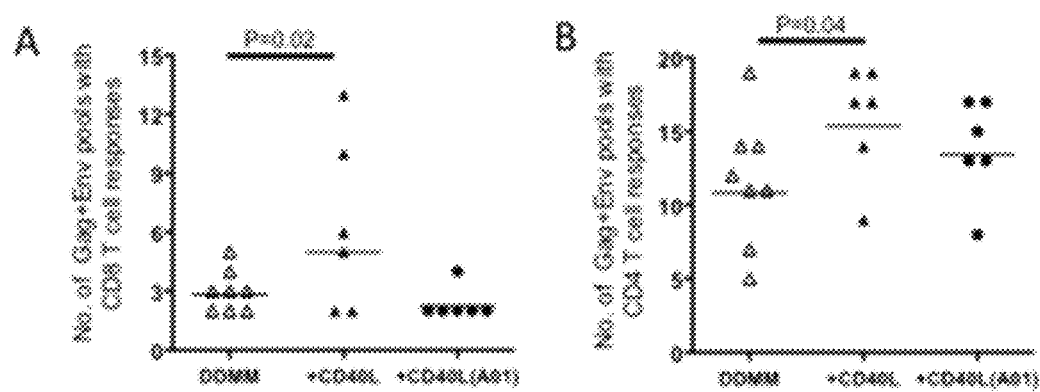
FIG. 3 shows data on anti-SW T cell responses post-vaccination and breadth of anti-SIV A) CD8 or B) CD4 T cell responses. Breadth is measured as the number of Gag or Env peptide pools that show positive IFNγ+ T cell responses. A total of 11 Gag peptide pools and 13 Env peptide pools were examined.

The animals that received CD40L DNA vaccine had higher titers of binding antibodies to the immunogen Env (SIV-mac239)(FIG. 2A) and higher levels of neutralization titers to a difficult to neutralize heterologous SIV Env (SIVsmE660) (FIG. 2C) than animals that received DNA vaccine. The CD40L DNA vaccine also generated anti-SIV Env antibody with higher levels of avidity than the DNA vaccine. This was true for against both immunogen Env (FIG. 2D) and challenge virus Env (FIG. 2E). In addition, animals immunized with CD40L DNA had a broader range of CD8 (FIG. 3A) and CD4 (FIG. 3B) T cell responses against multiple pools of SW Gag and Env peptides.

Figure 4:
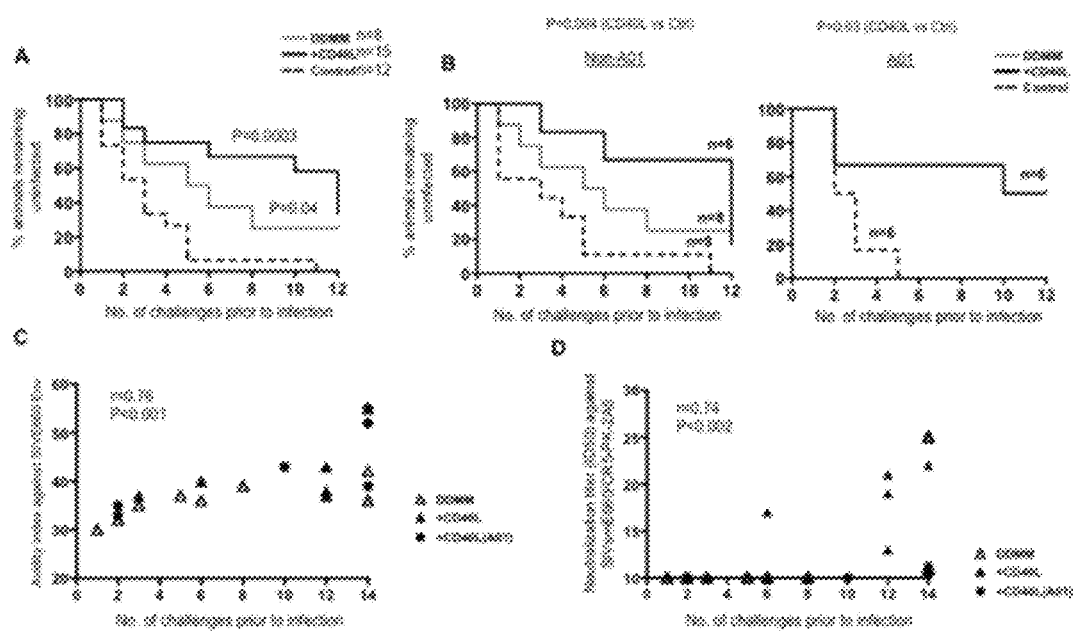
FIG. 4 shows data in a Kaplan-Meier's survival curve analysis post SIVsmE660 challenge. A) Survival curve of all macaques from DNA-only (DDMM), DNA-CD40L (+CD40L) and control groups. B) Survival curve of vaccinated and control groups according to their Mamu A*01 (A01) status. Note that all animals in the DDMM group are Mamu A*01 negative. C) Correlation between antibody avidity index against SIVsmE660 and acquisition of virus infection (no. of challenges prior to infection). A significant correlation ($r=0.76$, $P<0.001$) was observed. D) Correlation between neutralization titers against tier 2 isolate and acquisition of virus infection (no. of challenges prior to infection). A significant correlation ($r=0.74$, $P<0.002$) was observed. For C and D: animals that remained SIV negative at the end of 12 challenges are indicated at challenge 14. Spearman's rank correlation method was used for nonparametric data correlations.

5 months after the last MVA immunization, our vaccinated macaques were challenged with 12 weekly intrarectal doses of SIVsmE660. We also included 15 unvaccinated macaques as controls. Up to the 11th challenge, protection was seen of nearly ~60% against acquisition of SW infection in the CD40L group (FIG. 4). Here, only 5 out of 12 macaques became SIV-infected. However, 3 more macaques became infected at the last challenge. A significant positive association was observed between the avidity of anti-E660 Env antibody and decreased acquisition of infection (FIG. 4C).

Figure 5:
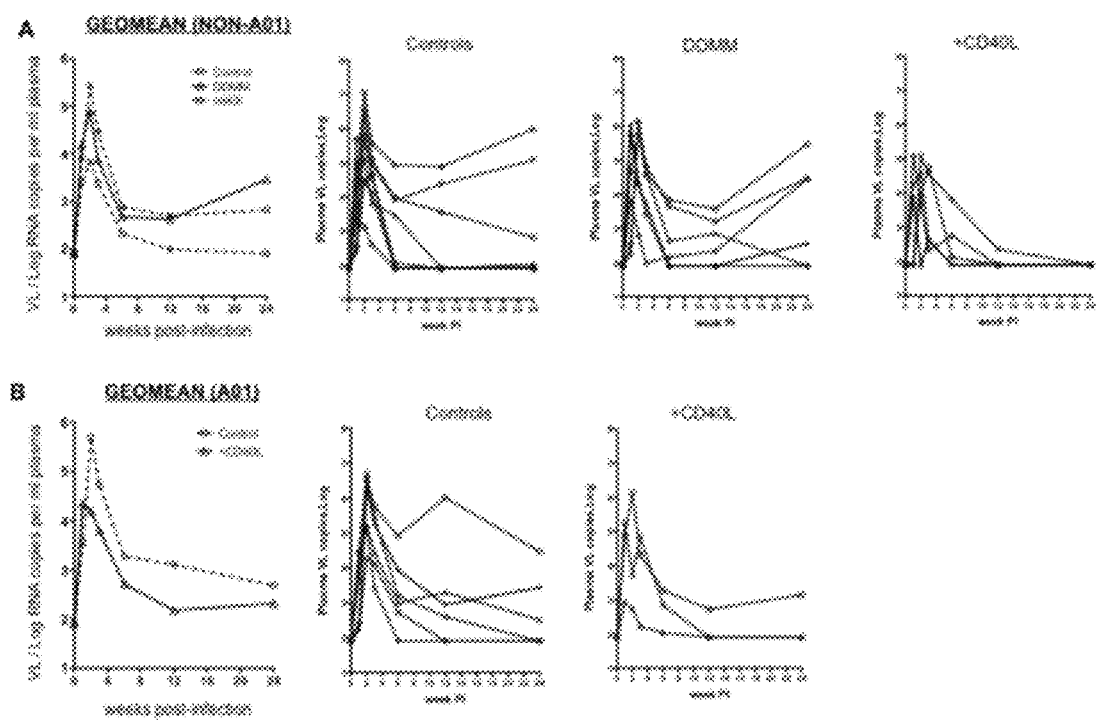
FIG. 5 shows data for certain embodiments of the disclosure. A) Plasma viral load of non-A01 or B) A01+ infected animals. Charts show the geomean data from each group (non-A01 or A01) and data from individual animals.
Figure 6:
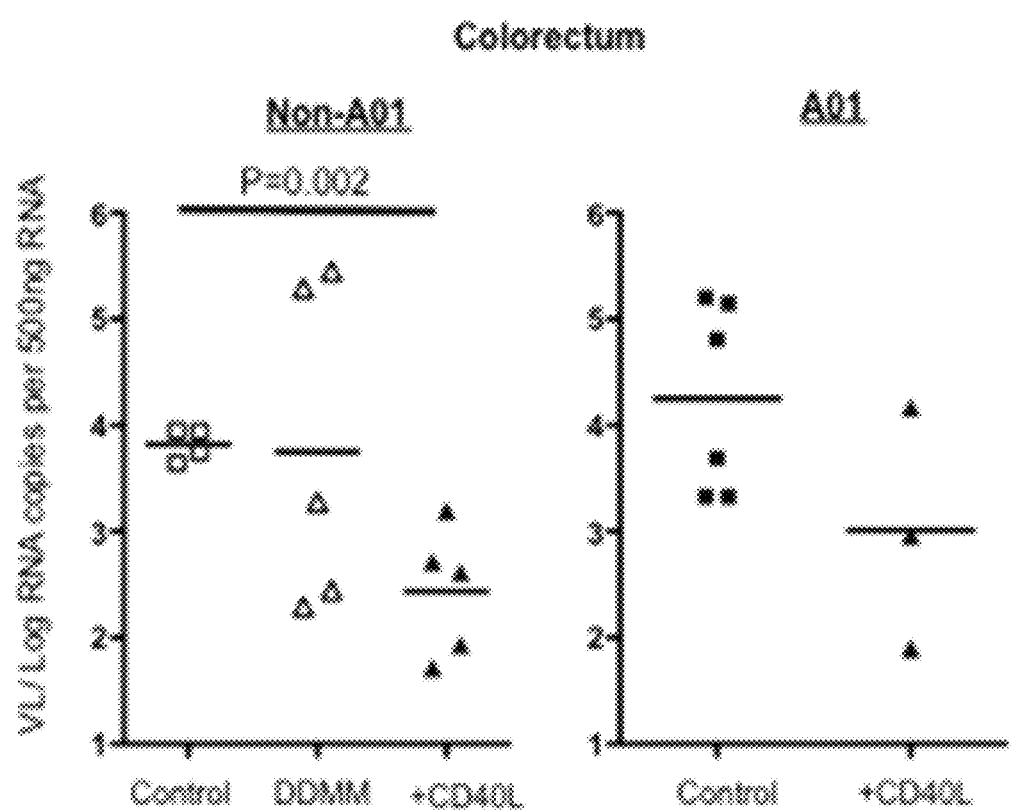
FIG. 6 shows data on levels of virus RNA copies in the colorectum of non-A01 and A01+ infected animals at 2 weeks post infection.

Among the macaques that were infected, significantly lower plasma viral load was seen at week 2 post-infection in the CD40L group than the control group (P=0.03) (FIGS. 5 and 6). Furthermore the levels of virus in the colorectal tissues were significantly lower in the CD40L group than the control group (P=0.002).

---

The invention claimed is:

1. A recombinant vector comprising genes sufficient to produce a viral like particle and a deoxyribonucleic acid sequence, wherein the deoxyribonucleic acid sequence transcribes into mRNA that encodes a lentiviral envelope protein followed by an internal ribosome entry site sequence operably linked to a sequence encoding CD40L.

2. The recombinant vector of claim 1, wherein the lentiviral envelope protein is a HIV envelope protein.

3. The recombinant vector of claim 1, further comprising a nucleic acid that encodes a viral matrix protein or a viral core protein.

4. The recombinant vector of claim 1, further comprising a nucleic acid that encodes a reverse transcriptase, proteases, ribonuclease or integrase.

5. The recombinant vector of claim 1, further comprising a gag or pol viral gene.

6. The recombinant vector of claim 1, further comprising a tat or rev viral gene.

* * * * *